United States Patent
Rudischhauser

(10) Patent No.: US 6,328,691 B1
(45) Date of Patent: Dec. 11, 2001

(54) ENDOSCOPE WITH AT LEAST ONE GLUED AND ADDITIONALLY WELDED END WINDOW

(75) Inventor: Jürgen Rudischhauser, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/230,500

(22) PCT Filed: Jul. 28, 1997

(86) PCT No.: PCT/DE97/01591

§ 371 Date: Nov. 23, 1999

§ 102(e) Date: Nov. 23, 1999

(87) PCT Pub. No.: WO98/04948

PCT Pub. Date: Feb. 5, 1998

(30) Foreign Application Priority Data

Jul. 26, 1996 (DE) .............................. 196 30 090
Oct. 28, 1996 (DE) .............................. 196 44 729

(51) Int. Cl.[7] ........................................ A61B 1/06
(52) U.S. Cl. ........................................ 600/176; 600/133
(58) Field of Search ..................... 600/162, 163, 600/169, 133, 176

(56) References Cited

U.S. PATENT DOCUMENTS

| 4,779,613 | * | 10/1988 | Hashiguchi et al. ............. 128/6 |
| 4,916,534 | | 4/1990 | Takahashi et al. . |
| 5,188,092 | * | 2/1993 | White ............................. 128/4 |
| 5,536,244 | * | 7/1996 | Muller et al. ................. 600/176 |
| 5,599,278 | * | 2/1997 | Hibbard ......................... 600/133 |
| 5,842,972 | * | 12/1998 | Wulfsberg ..................... 600/167 |

FOREIGN PATENT DOCUMENTS

| 3740417 A1 | 6/1989 | (DE) . |
| WO 95/24857 | 9/1995 | (WO) . |

* cited by examiner

*Primary Examiner*—Linda C. M. Dvorak
*Assistant Examiner*—Jocelyn Ram
(74) *Attorney, Agent, or Firm*—St.Onge Steward Johnston & Reens LLC

(57) ABSTRACT

The invention discloses an endoscope having an outer tube in whose distal end area are mounted an endoscope objective whose image is transmitted by an image transmitter to the proximal end of the endoscope, and a distal end window which closes the outer tube in a fluid- and gas-tight manner, and through which the path of the rays of the endoscope objective runs. The disclosed endoscope is characterized in that the distal end window and/or the proximal eyepiece window are glued in a manner known per se by their rim into the outer tube, the eyepiece cup or an adapter set into the outer tube or eyepiece cup, and in that a solderable ring-shaped layer is applied on at least one end surface of the end window for additionally joining the end window to the outer tube or adapter by means of a soldering layer.

21 Claims, 1 Drawing Sheet

ENDOSCOPE WITH AT LEAST ONE GLUED AND ADDITIONALLY WELDED END WINDOW

TECHNICAL FIELD

This invention refers to an endoscope wherein a distal end window has at least one surface provided with a solderable layer.

This invention refers to an endoscope with the features given in the preamble of claim 1.

BACKGROUND ART

Endoscopes of the present type are generally known with both rigid and flexible designs and are used not only for examining cavities, for instance in motors and turbines, but also in medicine for diagnostic or therapeutic purposes. Since endoscopes in operation are frequently used in cavities filled with often aggressive fluids or in cavities with high humidity, it is necessary for the distal end window to close the outer tube, in which the endoscope's optical system is disposed, in a fluid- and gas-tight manner.

Stringent demands are made on this fluid-and gas-tight juncture of the end window to the outer tube, since the outer tube with the end window can not only be located in aggressive media, but it can also be exposed to high temperatures. Especially in the case of medical endoscopes the connection of the end window to the outer tube is subjected to severe stress by being placed in a sterilizing solution and/or by being sterilized by hot steam at approximately 140° C. in an autoclave. The proximal eyepiece window undergoes the same hard treatment as the distal end window during the sterilization procedure.

In most known endoscopes the end windows are glued into the outer tube or the eyepiece cup. However, experience has shown that adhesions age and become leaky particularly when exposed to fluctuating temperatures and additionally to aggressive media. After a certain operating time moisture and/or fluids can penetrate into the endoscope.

For this reason, a proposal according to DE 37 40 417 A1 is to mount a metallic film on the peripheral surface of the distal end window and to solder this metallic film to the outer tube, which generally consists of a noncorrosive metal.

A so-called "close-joint soldering" is required for this. However, it is very difficult to check for faults, etc. in the soldering layer created in a close-joint soldering process. For this reason, in serial production it is possible to overlook faults in the joint, the result of this being that after a certain time the end window of the endoscope no longer has a fluid-tight seal.

DISCLOSURE OF THE INVENTION

The object of the invention is to further develop an endoscope of the type described above in such a manner that the end window or windows is/are securely joined to the outer tube or the eyepiece cup so as to be fluid tight, in a manner which can be easily checked.

According to the invention the distal end window and/or the eyepiece are glued in a manner known per se by their rim into the outer tube, the eyepiece cup or an adapter set into the outer tube or eyepiece cup. In addition, a ring-shaped layer suitable for soldering is applied to at least one end surface of the window or windows, preferably to the end surface facing the interior, for additionally joining the window to the outer tube, the eyepiece cup, or the adapter by means of a solder layer.

Thus, two joints independent of one another are provided in accordance with the invention, so that even if one of the connections is damaged or improperly produced, the endoscope stays fluid and gas tight regardless of extreme operating conditions.

Furthermore, the chemical resistance is increased over that of known endoscopes.

The gap gluing provided here in a manner that is known per se is relatively simple to carry out and to check as compared to a close-joint soldering process. Contrary to the close-joint soldering proposed in DE 37 40 417 A1, the additional, soldered joint is provided on an outer surface. For this reason, not only is it easily produced, but the resulting soldered joint can also be visually checked in a simple and reliable manner.

To create the disclosed connection, the soldered joint is preferably produced first. The gap gluing follows. If soldered joints are provided on both end surfaces, the soldered joint on the proximal end surface, i.e. the one facing the interior, is preferably produced first. Then the gluing and subsequently the soldering on the distal end surface are carried out. With this procedure the individual connections can easily be checked visually.

At any rate, the joint according to the invention has the advantage that the end window can be thinner than in the prior art without detracting from the quality of the connection between the end window and the outer tube.

By the use of two different connecting techniques the transfer of forces is more favorable than with only one connecting technique, particularly where thermally induced stresses are involved.

If an adapter is used, it can be connected or attached to the outer tube and/or the eyepiece cup in a variety of manners. Aside from the use of known connecting techniques, it is especially possible to attach the adapter in the outer tube or the eyepiece cup in accordance with the invention in the same manner in which the window is attached.

The connection according to the invention is suitable for endoscopes in any field of use and for any angle of vision.

The solderable layer applied to a surface of the end window is preferably a metallic layer which is applied by vacuum metallization or deposited electrolytically or by immersion. The soldered joint is preferably formed from a hard solder.

The melting temperature of the solder used and the softening temperature of the glue can be selected depending on the field of use of the endoscope. In the case of medical endoscopes to be sterilized by autoclaving, these selected temperatures must of course be high enough that the connecting layers are not damaged by the temperatures used in the sterilization process.

This condition is met, for example, if a solder that melts at a temperature substantially above the autoclaving temperature (approx. 140° C.) and a UV-hardenable glue are used.

The distal end window can consist in a known manner of quartz glass, BK 7, or a sapphire material, for example.

The disclosed procedure of applying the solder layer not to the peripheral surface as in the prior art, but rather to one or both end surfaces, has the added advantage that the ring-shaped layer produced can simultaneously serve as an aperture diaphragm or as a scattered-light diaphragm of the endoscope objective.

BRIEF DESCRIPTION OF DRAWINGS

The invention is described in detail below on the basis of a preferred embodiment with reference to the drawings.

BEST MODE OF CARRYING OUT THE INVENTION

Figure 1:
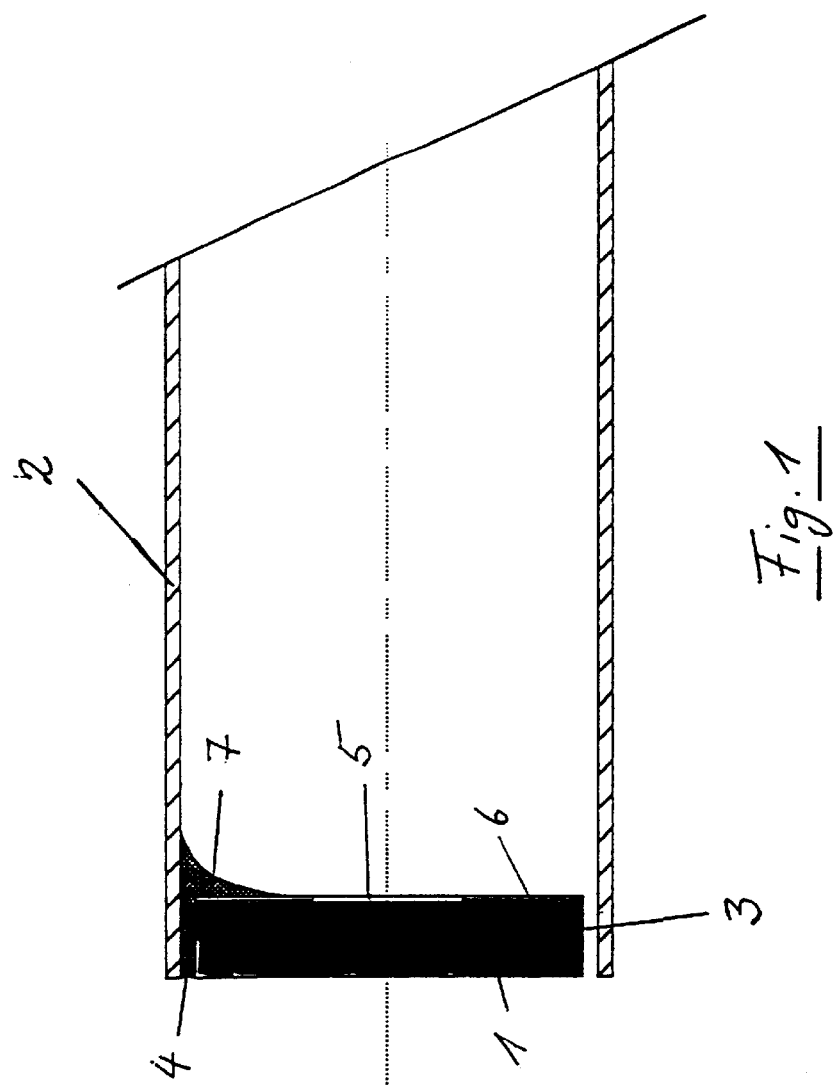
FIG. 1 shows a longitudinal section through the distal end area.

FIG. 1 shows a longitudinal section through the distal end of an endoscope. Reference number 1 refers to a distal end window which, for example, can be made of quartz glass, BK7, or a sapphire material. The end window is set into an outer tube 2 which accommodates the endoscope's optical system, which is not shown here, namely an objective lens and an image transmitter. The optical system can comprise an array of relay lens systems or an optical fiber bundle. The outer tube consists, for example, of Monel® or of a VA steel with suitable corrosion-resistant properties.

A layer of glue 4 which can especially consist of a UV-hardenable glue is located between the peripheral surface 3 of the end window 1 and the outer tube 2. In addition, a ring-shaped solderable layer 6 which particularly can be a metallic layer is applied onto the proximal end surface 5 of the end window 1. The end window 1 is connected to the outer tube 2 via the solderable ring-shaped layer 6 by means of a soldered joint 7.

Figure 2:
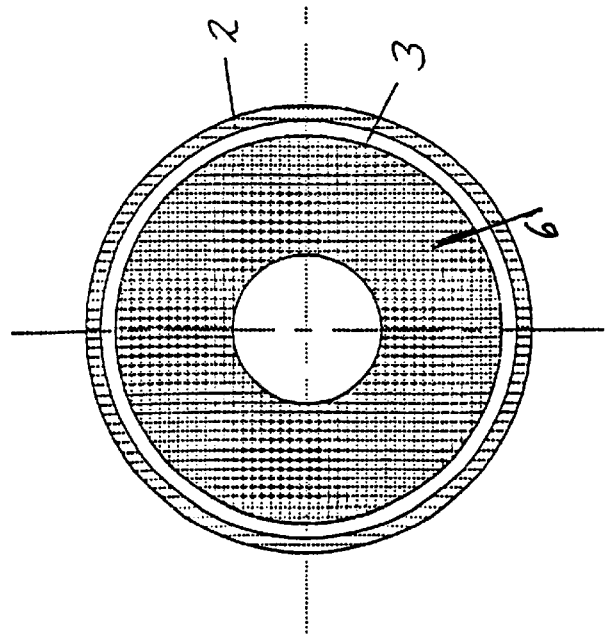
FIG. 2 shows a plan view of the distal end area o f an endoscope according to the invention.

FIG. 2 shows a plan view of the end window in which the gap to be filled with glue between the end window 1 and the outer tube 2 is clearly visible.

The same procedure applies for the eyepiece window.

The inventive concept of providing an end-face soldered joint in addition to a peripheral gluing can be implemented in flexible or rigid endoscopes. However, it is particularly advantageous in rigid endoscopes, as they have a solderable outer tube usually consisting of Monel. In flexible endoscopes an adapter may be necessary.

What is claimed is:

1. An endoscope with an outer tube in whose distal end area are mounted an endoscope objective lens whose image is transmitted by an image transmitter to the proximal end of the endoscope, and a distal end window which closes the outer tube in a fluid-tight and gas-tight manner, and through which the path of the rays of the endoscope objective lens runs, characterized in that the distal end window and/or an eyepiece window are glued by their rim into the outer tube or an eyepiece cup, respectively, or an adapter set into the outer tube or eyepiece cup, respectively, and in that a ring-shaped solderable layer is applied on at least one surface of the end window for additionally joining the end window to the outer tube or adapter by means of a soldering joint formed between the ring-shaped solderable layer and the outer tube or the adapter.

2. The endoscope according to claim 1, characterized in that the solderable ring-shaped layer is applied on an inner surface of the end window.

3. The endoscope according to claim 1, characterized in that solderable ring-shaped layers are applied on opposite surfaces of the end window.

4. The endoscope according to claim 1, characterized in that the solderable layer is a metallic layer applied by vacuum metallization.

5. The endoscope according to claim 1, characterized in that the melting temperature of the soldering joint and a softening temperature of a glue are sufficiently high so that the endoscope can be sterilized by autoclaving.

6. The endoscope according to claim 5, characterized in that the glue is a UV-hardenable glue.

7. The endoscope according to claim 1, characterized in that the soldering joint is a hard solder.

8. The endoscope according to claim 1, characterized in that the end window consists of quartz glass or BK7.

9. The endoscope according to claim 1, characterized in that the end window consists of a sapphire material.

10. The endoscope according to claim 1, characterized in that the ring-shaped solderable layer applied to a surface of the end window forms an aperture or a stray light screen of the endoscope objective lens.

11. The endoscope according to claim 1, characterized in that the outer tube consists of a noncorrosive metal.

12. An endoscope with an outer tube in whose distal end area are mounted an endoscope objective lens whose image is transmitted by an image transmitter to a proximal end of the endoscope, and a proximal end eyepiece window which closes the outer tube in a fluid-tight and gas-tight manner, and through which a path of rays from the endoscope objective lens image runs, characterized in that the proximal end eyepiece window is glued into the outer tube, and in that a ring-shaped solderable layer is applied on at least one end surface of the proximal end eyepiece window for additionally joining the proximal end eyepiece window to the outer tube by a soldering layer.

13. The endoscope according to claim 12, characterized in that the solderable ring-shaped layer is applied on an inner surface of the proximal end eyepiece window.

14. The endoscope according to claim 12, characterized in that solderable ring-shaped layers are applied on opposite end surfaces of the proximal end eyepiece window.

15. The endoscope according to claim 12, characterized in that a melting temperature of the soldering layer and a softening temperature of a glue are sufficiently high that the endoscope can be sterilized by autoclaving.

16. The endoscope according to claim 15, characterized in that the glue is a UV-hardenable glue.

17. The endoscope according to claim 12, characterized in that the soldering joint is a hard solder.

18. The endoscope according to claim 12, characterized in that the end eye-piece consists of quartz glass or BK7.

19. The endoscope according to claim 12, characterized in that the end eye-piece consists of a sapphire material.

20. A method of manufacturing an endoscope having an outer tube with a distal end in which an endoscope objective lens is mounted;

a distal end window having a peripheral rim glued into either said outer tube or a first adapter set into said outer tube;

a proximal end in which an eyepiece is mounted in an eyepiece cup;

a proximal end window having a peripheral rim glued into either said eyepiece cup or a second adapter set into said eyepiece cup;

comprising the steps of applying an annular solderable layer on at least one surface of said distal end window or said proximal end window;

joining said solderable layer of said distal end window to said outer tube or first adapter, or joining said solderable layer of said proximal end window to said eyepiece cup or said second adapter by means of an annular soldering joint, leaving a gap between the peripheral surface of the distal end window and the outer tube or first adapter, or the peripheral surface of said proximal end window and the eyepiece cup or second adapter; and filing said gap with glue.

21. A method of manufacturing an endoscope according to claim 20, characterized by applying said annular solderable layer to both surfaces of said distal end window or said proximal end window, producing a soldered joint first on the surface of said window facing the interior of said outer tube, then performing the gluing, and subsequently performing the soldering on the outer end surface of said window.

* * * * *